United States Patent [19]

Uematsu et al.

[11] Patent Number: 4,935,117

[45] Date of Patent: Jun. 19, 1990

[54] FLOW THROUGH TYPE ION ELECTRODE

[75] Inventors: Hiroaki Uematsu; Kunio Terada, both of Miyanohigashi, Japan

[73] Assignee: Horiba, Ltd., Kyoto, Japan

[21] Appl. No.: 370,449

[22] Filed: Jun. 23, 1989

[30] Foreign Application Priority Data

Jun. 29, 1988 [JP] Japan .................. 63-86186

[51] Int. Cl.$^5$ .............................................. G01N 27/30
[52] U.S. Cl. ....................................... 204/411; 204/409
[58] Field of Search ................................. 204/409, 411

[56] References Cited

U.S. PATENT DOCUMENTS

| 4,404,065 | 9/1983 | Matson | 204/1 T |
| 4,556,473 | 12/1985 | Kohno et al. | 204/409 |
| 4,758,325 | 7/1988 | Kanno et al. | 204/411 |
| 4,797,191 | 1/1989 | Metzner et al. | 204/411 |

OTHER PUBLICATIONS

H. F. Osswald et al., Chimia, 31, (1977) Nr. 2.

Primary Examiner—G. L. Kaplan
Attorney, Agent, or Firm—Price, Gess & Ubell

[57] ABSTRACT

A flow through type ion electrode apparatus including a number of interconnectable block structures. Each block structure includes recesses in respective faces thereof, which lead to a through hole extending between the faces. A membrane electrode is located within each block structure so as to communicate with the through hole. A spacer having a through hole therein is inserted in a recess of each of a pair of adjacent block structures to interconnect the adjacent block structures.

17 Claims, 4 Drawing Sheets

Fig. 1
Fig. 2
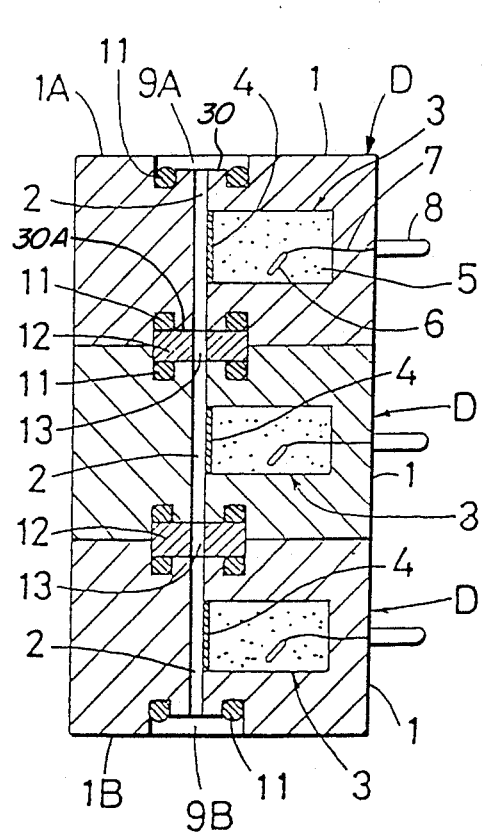
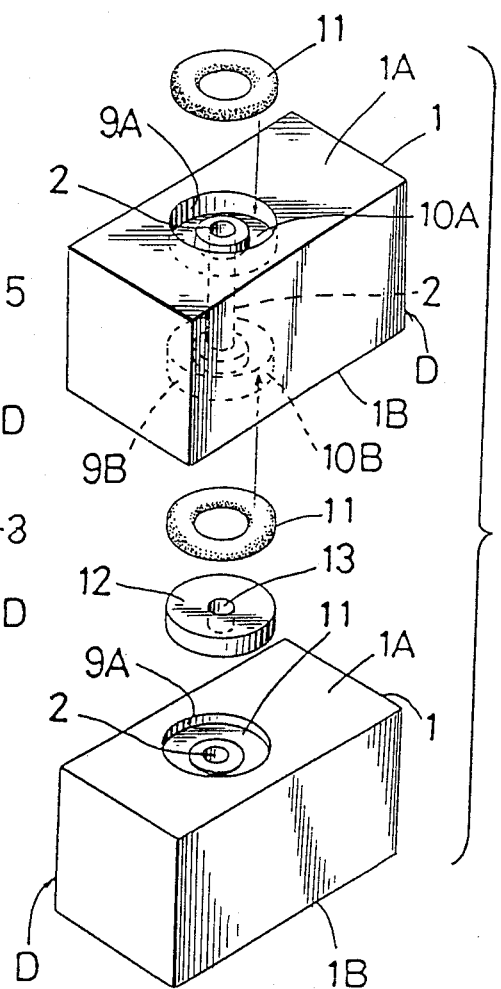

FLOW THROUGH TYPE ION ELECTRODE

BACKGROUND OF THE INVENTION

1. Field of the Invention

The present invention relates to a flow through type ion electrode.

2. Description of Related Art

In order to measure a sample by means of a plurality of flow through type electrodes, the prior art has employed a flow through type cell 50 having a through hole 51 for passing the sample therethrough, as shown in FIG. 7. The cell 50 is provided with a plurality of holes 52 formed adjacent to, i.e., in the direction facing and meeting at right angles with the through hole 51, so that electrodes 54 having a sensitive membrane 53 may be mounted in the holes 52.

The installation and detachment of the prior art electrodes 54 are troublesome, and cap rings 55 and sealing members 56, such as packing, for fixedly mounting the electrodes 54 have been required, resulting in a multiplicity of parts and increased cost.

SUMMARY OF THE INVENTION

The present invention has been achieved paying attention to the above-described matters, and it is an object of the present invention to provide an easily operable flow through type ion electrode which is simple in construction and inexpensive.

In order to achieve the above-described object, a block member is provided having a through hole for passing a sample therethrough and a membrane electrode disposed adjacent the through hole. Recesses are formed in the block member to communicate with the through hole so that a plurality of such block members may be interconnected to each other by means of spacer conduits inserted in the recesses.

The structure resulting from the invention is simple and inexpensive, and the block members can be easily interconnected and separated, thereby achieving the objects of the invention.

BRIEF DESCRIPTION OF THE DRAWINGS

A first preferred embodiment of the present invention is shown in FIGS. 1 and 2, in which:

FIG. 1 is a longitudinal sectional view showing three interconnected flow through type ion electrodes; and FIG. 2 is an exploded perspective view of two interconnected flow through type ion electrodes.

DESCRIPTION OF THE PREFERRED EMBODIMENTS

Figure 3:
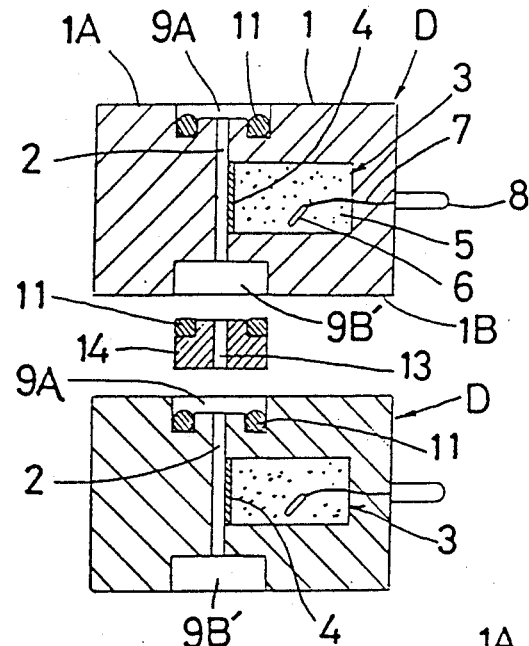
FIG. 3 is a longitudinal sectional view showing a second preferred embodiment of the present invention.

The preferred embodiments of the present invention will be described below with reference to the drawings.

FIGS. 1 and 2 show a flow through type ion electrode according to the first preferred embodiment of the present invention. In particular, FIG. 1 is a longitudinal sectional view illustrating three connected flow through type ion electrodes. FIG. 2 is an exploded perspective view showing two connected flow through type ion electrodes.

Referring now to FIGS. 1 and 2, "D" designates a flow through type ion electrode and reference numeral 1 designates a block member forming part of the flow through type ion electrode D. The block member 1 is formed of a suitable synthetic resin and has a cross-sectional outer periphery in the form of, for example, a rectangle. The block member 1 is provided with a through hole conduit 2 having, for example, a circular cross-section. The through hole conduit 2 extends from one end face 1A of the block member 1 to the other end face 1B of the block member 1. Each block member 1 also includes a membrane electrode 3.

The through hole 2 conducts a sample through the device, and the membrane electrode 3 measures a specified ion (or gas or enzyme) contained in the sample flowing through the hole 2. The membrane electrode 3 is formed, for example, in the following manner. A hole (not shown) having a selected size is formed in a direction at right angles with the through hole 2 so as to communicate with the through hole conduit 2, and a thin sensitive membrane 4 formed of, for example, high molecular material is extended over the bottom of this hole so as to lie adjacent the through hole 2. Then, a selected quantity of a KCl electrolyte solution 5 and an internal element 6 formed of Ag/AgCl are disposed in the hole. The internal element 6 is then connected with an outside junction 8 by means of a lead wire 7. Thereafter, a portion of the hole is filled with the same synthetic resin as that of which the block member 1 is formed, thereby encasing the electrolyte 5 and the internal element 6.

Reference numerals 9A, 9B designate generally cylindrical recesses of suitable depth formed at both end faces 1A, 1B of the block member 1 concentrically with the through hole conduit 2. Both recesses 9A, 9B have the same size and are provided with grooves 10A, 10B for mounting sealing members therein about central protrusion members 30, 30A extending into the respective spaces of the recesses 9A and 9B. The sealing members 11, such as O-rings, are mounted in the grooves 10A, 10B.

Reference numeral 12 designates a disk spacer provided with a hole 13 communicating with the through hole conduit 2 (for example, a circular hole having the same diameter as the through hole 2) at the center thereof. The outside diameter of this spacer 12 is nearly equal to the diameter of the recesses 9A, 9B. In addition, the thickness of the spacer 12 is equal to the sum of depths of the recesses 9A, 9B. The spacer 12 is formed of, for example, synthetic resin, so as to have suitable elasticity.

In order to interconnect the respective flow through type ion electrodes having the above-described construction, the sealing member 11 is first placed in the groove 10A within the recess 9A on the end face 1A of one flow through type ion electrode D. The spacer 12 is then placed in the recess 9A in which the sealing member 11 was inserted. Under this condition, the spacer 12 projects over the end face 1A by a length equal to one-half the thickness thereof. Subsequently, the recess 9B formed on the end face 1B of another flow through type ion electrode D is placed on the projected portion of the spacer 12, thereby interconnecting two flow through type ion electrodes D. The above-described procedure is repeated to interconnect a plurality of flow through type ion electrodes D, under the condition that the through holes 2 conductively connect with the holes 13 of the spacers 12, as shown in FIG. 1. In addition, in order to separate the interconnected flow through type ion electrodes D, a force is applied to the flow through type ion electrode D along the axis of the through hole 2 to pull apart the flow through type ion electrodes D.

According to the above construction, a plurality of ingredients contained in one sample can be measured by interconnecting a plurality of flow through type ion electrodes D, each electrode D having a membrane 4 of different sensitivity.

Although the recesses 9A, 9B formed on both end faces 1A, 1B of the block member 1 are provided with sealing members 11 formed separately from the spacer 12 in the above-described first preferred embodiment, the present invention is not limited by the first preferred embodiment; rather, various kinds of modifications can be made.

FIG. 3 shows the second preferred embodiment of the present invention, in which a recess 9A having the same construction as in the above-described first preferred embodiment is formed on one end face 1A of the block member 1. The second preferred embodiment employs a recess 9B' formed in the end face 1B having no groove, but rather having a depth slightly larger than that of the recess 9A and a diameter the same as that of the recess 9A. Additionally, in this second embodiment, a spacer 14 is provided with a hole 13, an outside diameter equal to the inside diameter of the recesses 9A and 9B', and a thickness nearly equal to the sum of depths of the recesses 9A and 9B'. A sealing member 11 is fixedly mounted on an annular extension formed on the spacer 14 by means of adhesives or the like.

In order to interconnect, for example, two flow through type ion electrodes D, according to the second preferred embodiment, the spacer 14 is placed in the recess 9B' so that the end of the spacer 14 bearing the sealing member 11 engages the bottom of the recess 9B' of one flow through type ion electrode D, while the opposite end of the spacer 14 engages the recess 9A of the second flow through type ion electrode D.

Figure 4:
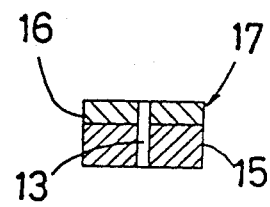
FIG. 4 is a longitudinal sectional view showing a spacer according to a third preferred embodiment of the present invention.

FIG. 4 shows a third preferred embodiment of the present invention, in which a spacer 17 is formed of, for example, Hytrel ™, which is a polyester elastomer manufactured by TORAY-DUPONT. This spacer 17 provides both the spacer function and the sealing function due to its rubber elasticity. The spacer 17 of FIG. 4 is integrally formed of a spacer portion 15 and a sealing material portion 16, and is used with a flow through type ion electrode D the same as that used in the above-described second preferred embodiment.

Figure 5:
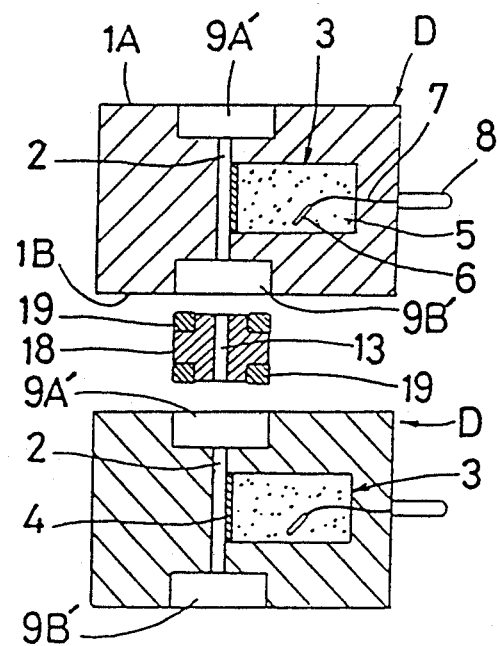
FIG. 5 is a longitudinal sectional view showing a fourth preferred embodiment of the present invention.

FIG. 5 shows a third preferred embodiment of the present invention in which a block member 1A is provided with recesses 9A', 9B', neither of which has a groove. Sealing members 19 are fixedly mounted on annular extensions formed at either end of a spacer 18.

In addition, the relation between the dimensions of the spacers 17, 18 and the dimension of the recessed portions 9A', 9B' shown in FIGS. 4 and 5 are similar to the dimensional relation in the above-described first or second preferred embodiments.

Figure 6:
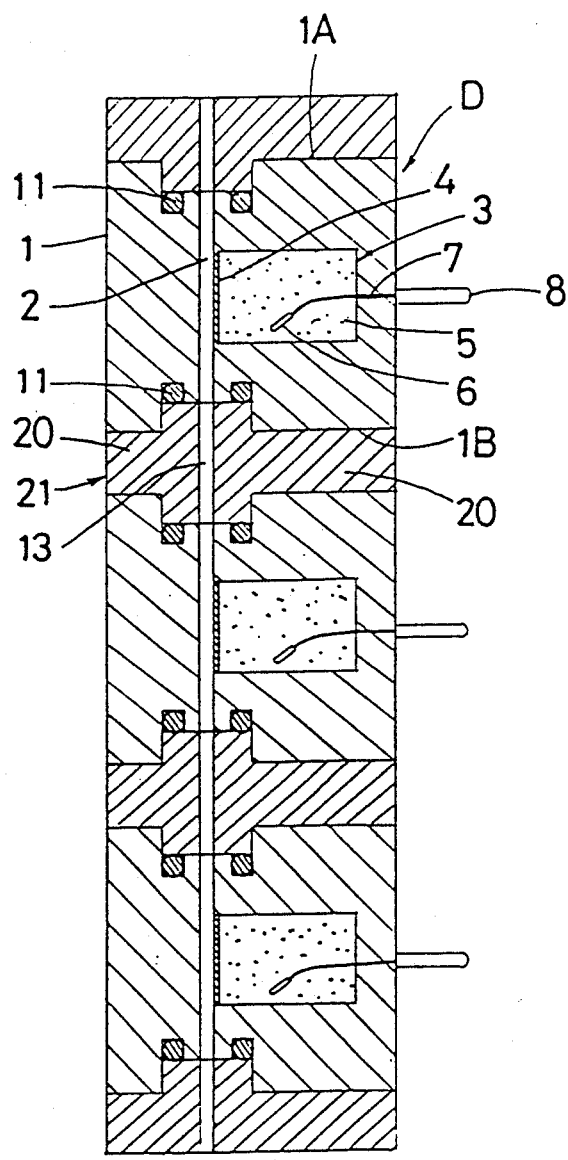
FIG. 6 is a longitudinal sectional view showing a fifth preferred embodiment of the present invention.
Figure 7:
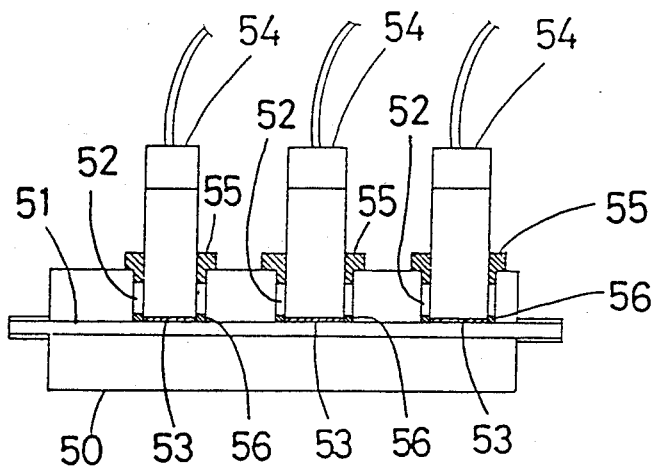
FIG. 7 is a sectional view describing a prior art ion electrode.

Although the spacers 12, 14, 17, 18 are all formed so as not to be engaged with the end faces 1A, 1B, which are connecting faces of the block member 1, in the above-described first to fourth preferred embodiments, a spacer 20 may have a construction so as to have a portion 21 engaged with the entire surface of the end faces 1A, 1B as in the fifth preferred embodiment shown in FIG. 6. In this case, the flow through type ion electrodes D can be connected to each other without producing any strain on the connecting faces.

The above-described sealing members 11, 16, 19 are formed of materials having superior sealing capacity such as silicon rubber. In addition, although they are not shown, the spacers 12, 14, 17, 18 themselves may be formed of members having a superior sealing capacity. In this case, the construction of the connecting portions is simplified.

As described above, a block member of the flow through type ion electrode according to the present invention is provided with a through hole for passing the sample therethrough, a membrane electrode facing the through hole therewithin, and recesses formed so as to encompass the through hole at both end faces thereof so that several block members may be connected to each other through spacers having a hole leading to the through hole and placed in the recesses, such that the flow through type ion electrode according to the present invention is simple in construction and inexpensive and such that the block members can be easily connected to each other and separated.

What is claimed is:

1. A flow through type ion electrode apparatus comprising:
    a block member having first and second end faces and a through hole conduit extending between said first and second end faces;
    first and second recesses formed respectively in said first and second end faces so as to communicate with said through hole conduit, at least one of the recesses having a protrusion member extending from said block member, about said through hole conduit and into said recess space, and
    a membrane electrode formed within said block member and disposed adjacent said through hole conduit.

2. The apparatus of claim 1 further comprising:
    a second block member having first and second end faces and a through hole conduit therein extending between said first and second end faces;
    third and fourth recesses formed respectively between said first and second end faces of said second block member so as to communicate with the through hole conduit of said second block member, at least one of the recesses having a protrusion member extending from said block member about said through hole conduit and into said recess space;
    a membrane electrode formed within said second block member and disposed adjacent the through hole conduit of said second block member, and
    spacer means having a through hole therein and located in one of said first and second recesses and one of said third and fourth recesses for interconnecting said first and second block members.

3. The apparatus of claim 2 wherein at least one of said recesses has a groove in the bottom thereof formed about the protrusion member.

4. The apparatus of claim 3 further including a sealing means mounted in said groove for sealingly engaging said spacer means.

5. The apparatus of claim 2 wherein said spacer means includes at least one sealing means mounted thereon.

6. The apparatus of claim 5 wherein said sealing means comprises an elastomer integrally formed with said spacer means.

7. The apparatus of claim 1 further including a spacer member of a configuration to conform to the recess space provided at each end face and also covering the end face to enable a spacing of block members when connected with another block member.

8. A flow through type electrode apparatus for electrochemical testing of a sample and capable of interconnection with other electrode apparatus to provide testing by a plurality of electrode apparatus, comprising:
   a block member having first and second end faces and a conduit extending therethrough, a first and second recess positioned in the block member on the respective first and second end faces to provide a recess space about each opening of the conduit, a protrusion member extending from the block member into each recess space with the conduit extending through the protrusion members, and
   an electrode assembly mounted within the block member for operative communication with the conduit, whereby a series of block members can be interconnected through their end faces.

9. The apparatus of claim 8 further including a sealing member mounted about each protrusion member.

10. The apparatus of claim 8 further including a spacer member of a configuration to conform to the recess space provided at each end face.

11. The apparatus of claim 10 wherein the spacer member has a peripheral groove to support a sealing member.

12. The apparatus of claim 8 further including a spacer member of a configuration to conform to the recess space provided at each end face and also covering the end face to enable a spacing of block members.

13. A flow through type electrode apparatus for electrochemical testing of a sample and capable of interconnection with other electrode apparatus to provide testing by a plurality of electrode apparatus, comprising:
   a block member having first and second end faces and a conduit extending therethrough, a first and second recess positioned in the block member on the respective first and second end faces to provide a recess space about each opening of the conduit, a protrusion member extending from the block member into at least one of the recess spaces with the conduit extending through the protrusion member, and
   an electrode assembly mounted within the block member for operative communication with the conduit, whereby a series of block members can be interconnected through their end faces.

14. The apparatus of claim 13 further including a sealing member mounted about each protrusion member.

15. The apparatus of claim 13 further including a spacer member of a configuration to conform to the recess space provided at each end face.

16. The apparatus of claim 15 wherein the spacer member has a peripheral groove to support a sealing member.

17. The apparatus of claim 13 further including a spacer member of a configuration to conform to the recess space provided at each end face and also covering the end face to enable a spacing of block members.

* * * * *